US008282027B2

(12) United States Patent
Suda et al.

(10) Patent No.: US 8,282,027 B2
(45) Date of Patent: Oct. 9, 2012

(54) ELECTROSTATICALLY ATOMIZING DEVICE

(75) Inventors: Hiroshi Suda, Takatsuki (JP); Takayuki Nakada, Hikone (JP); Takahiro Miyata, Hirakata (JP); Masaharu Machi, Shijonawate (JP)

(73) Assignee: Panasonic Corporation, Osaka (JP)

( * ) Notice: Subject to any disclaimer, the term of this patent is extended or adjusted under 35 U.S.C. 154(b) by 419 days.

(21) Appl. No.: 12/303,073

(22) PCT Filed: May 22, 2007

(86) PCT No.: PCT/JP2007/060417

§ 371 (c)(1), (2), (4) Date: Dec. 1, 2008

(87) PCT Pub. No.: WO2007/145058
PCT Pub. Date: Dec. 21, 2007

(65) Prior Publication Data

US 2009/0184186 A1 Jul. 23, 2009

(30) Foreign Application Priority Data

Jun. 13, 2006 (JP) ................................ 2006-163867

(51) Int. Cl.
*B05B 5/03* (2006.01)
(52) U.S. Cl. ......................... 239/690; 422/292; 134/198
(58) Field of Classification Search .................. 134/198; 422/292; 239/690
See application file for complete search history.

(56) References Cited

U.S. PATENT DOCUMENTS

| | | | |
|---|---|---|---|
| 5,337,963 | A | 8/1994 | Noakes |
| 2004/0022675 | A1 | 2/2004 | An |
| 2004/0045909 | A1 | 3/2004 | Tomioka et al. |
| 2006/0130533 | A1 | 6/2006 | Ooe et al. |
| 2006/0164093 | A1 | 7/2006 | Ooe et al. |

FOREIGN PATENT DOCUMENTS

| | | | |
|---|---|---|---|
| CN | 1692081 | A | 11/2005 |
| EP | 0 486 198 | A1 | 5/1992 |
| EP | 1 580 313 | A1 | 9/2005 |
| FR | 2 527 049 | A1 | 11/1983 |
| JP | 05-345156 | A | 12/1993 |
| JP | 11-90446 | A | 4/1999 |
| JP | 11-167975 | A | 6/1999 |
| JP | 2001-286546 | A | 10/2001 |
| JP | 2003-079714 | A | 3/2003 |
| JP | 2004-524875 | A | 8/2004 |
| JP | 2005-7317 | A | 1/2005 |
| JP | 2005-164139 | A | 6/2005 |
| JP | 2005-269967 | A | 10/2005 |
| JP | 2005-270278 | A | 10/2005 |

(Continued)

OTHER PUBLICATIONS

Notification of Reasons for Refusal for the Application No. 2006-163867 from Japan Patent Office mailed Nov. 16, 2010.

(Continued)

*Primary Examiner* — Sean E Conley
(74) *Attorney, Agent, or Firm* — Cheng Law Group, PLLC

(57) ABSTRACT

An electrostatic atomizing device for ejecting a mist of charged minute particles includes metal ion elution means for eluting sterilizing metal ions into a liquid to be electrostatically atomized. The metal ions are taken up by the charged minute particles, and are ejected into an environment space together with the charged minute particles, thereby eliciting a sterilizing effect. The elution amount of the metal ions is regulated by varying the voltage applied between two kinds of metal bodies.

6 Claims, 3 Drawing Sheets

FOREIGN PATENT DOCUMENTS

JP    2005-296578 A    10/2005
JP    2006-7195 A    1/2006

OTHER PUBLICATIONS

Notification of the First Office Action for Application No. 20070021718.7 from State Intellectual Property Office of People's Republic of China dated Sep. 14, 2010.

International Search Report for the Application No. PCT/JP2007/060417 mailed Sep. 4, 2007.

Notification of Reasons for Refusal for the Application No. 2006-163867 from Japan Patent Office mailed Apr. 14, 2009.

Notification of Reasons for Refusal for the Application No. 2006-163867 from Japan Patent Office mailed Jan. 5, 2010.

Supplementary European Search Report for the Application No. EP 07 74 3851 dated Mar. 23, 2011.

Fig.5

ELECTROSTATICALLY ATOMIZING DEVICE

TECHNICAL FIELD

The present invention relates to an electrostatically atomizing device for generating a mist of charged minute particles having sterilizing power.

BACKGROUND

Japanese Patent Application Laid-open No. H05-345156 discloses a conventional electrostatically atomizing device for generating charged minute particles of nanometer size (nanometer-size mist). In the device, a high voltage is applied across an emitter electrode, supplied with water, and an opposed electrode, to induce Rayleigh breakup of the water held on the emitter electrode, thereby atomizing the water. Such charged minute water particles, long-lived and containing active species (radicals), diffuse throughout an environment space, adhering to and/or penetrating into objects present in the space, so that these objects can be effectively sterilized and deodorized as a result.

The mist of charged minute particles comprises active species (radicals), and hence the mist can potentially elicit a sterilizing and deodorizing effect on germs and harmful substances that are present in the environment space. Sterilization by the active species (radicals) contained in the mist of charged minute particles is the result of germs and harmful substances being engulfed by the charged minute water particles W during the flight of the mist of charged minute particles or when the mist of charged minute particles adheres to target objects. In consequence, the germ and harmful substance elimination effect is observed only during the flight or adhesion of the mist of charged minute particles. That is, the mist is effective against germs and harmful substances present in the space only at such times. This is problematic in that such elimination effect cannot be expected to work against new germs and harmful substances that develop on, or adhere to, objects in the space, once a certain time has elapsed since adhesion of the mist of charged minute particles onto the target objects. Also, there are cases in which the sterilizing effect of the active species contained in the mist of charged minute particles is insufficient for the environment in which the mist is used, where a greater sterilizing effect is thus required.

DISCLOSURE OF THE INVENTION

In the light of the above problems, it is an object of the present invention to provide an electrostatically atomizing device that can be expected to elicit a high sterilizing effect, also after generation of a mist of charged minute particles, so that a greater sterilizing effect can be achieved.

The electrostatically atomizing device according to the present invention includes metal ion elution means for eluting sterilizing metal ions into a liquid to be electrostatically atomized. This affords a high sterilizing effect, since sterilizing metal ions are thus added to the active species (radicals) inherently contained in the mist of charged minute particles that is generated through electrostatic atomization. Even after some time since adhesion of the charged minute particles to target objects, these metal ions persist at the adhesion sites long afterwards. These metal ions can sterilize as a result harmful substances and germs that become adhered subsequently.

Preferably, the electrostatically atomizing device of the present invention includes a tank for holding a volume of the liquid, and a carrier which is connected to the tank and to which the liquid is supplied. In this case, the carrier feeds the liquid to a discharge end, where the liquid is atomized by application of a high voltage and a mist of charged minute particles is ejected. Preferably, the metal ion elution means comprises a set of different metal bodies. The metal bodies are immersed into the liquid in the tank to generate a potential difference between the metal bodies, thereby the metal ions can be eluted. Metal ions can thus be brought into the liquid by way of a simple construction.

Preferably, one of the metal bodies that elutes the metal ions is selected from the group consisting of Ag, Zn and Cu.

Preferably, the metal ion elution means has a voltage applicator for generating a potential difference between two kinds of metal bodies. The sterilizing power can then be adjusted by varying the elution amount of metal ions through changes in the voltage applied between the metal bodies.

Also, the electrostatically atomizing device of the present invention preferably includes means for measuring conductivity of the liquid, such that the voltage applicator varies the voltage applied between the metal bodies in accordance with the measured conductivity. This allows bringing the elution amount of metal ions to a target value even if conductivity varies depending on the liquid used. A high sterilizing effect can be maintained as a result.

BRIEF DESCRIPTION OF THE DRAWINGS

Figure 5:
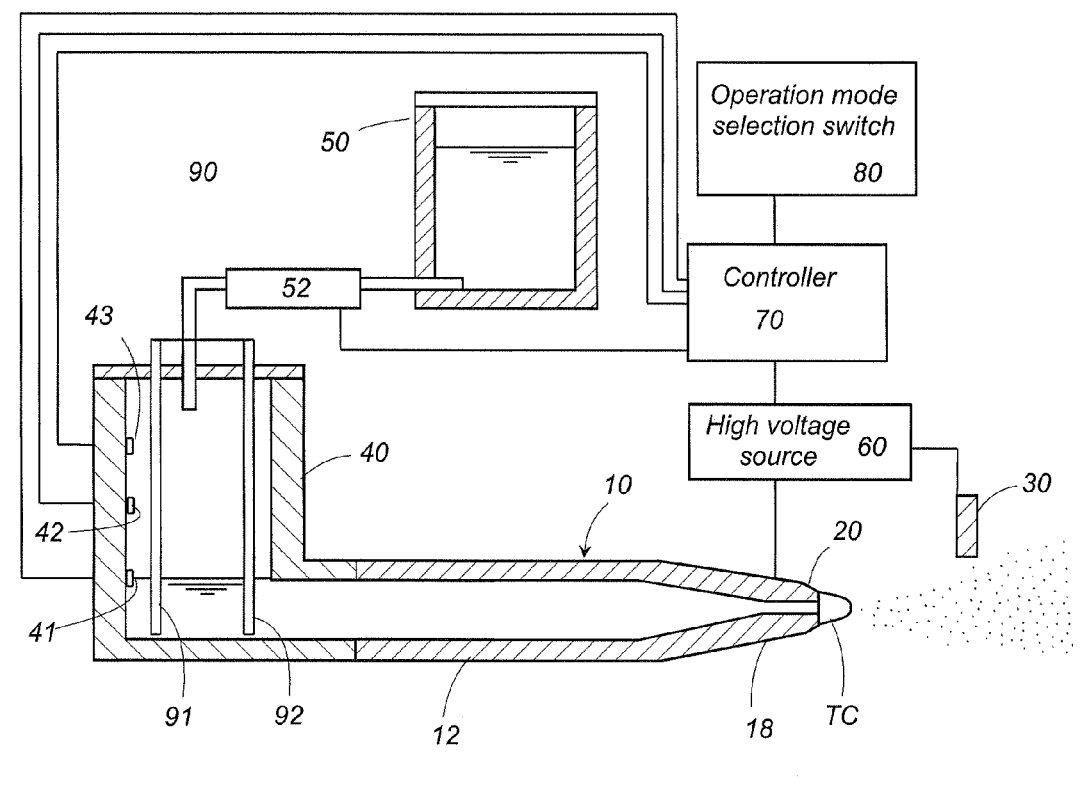

FIG. 5 is a schematic diagram illustrating another embodiment of the electrostatically atomizing device of the present invention.

BEST MODE FOR CARRYING OUT THE INVENTION

Figure 1:
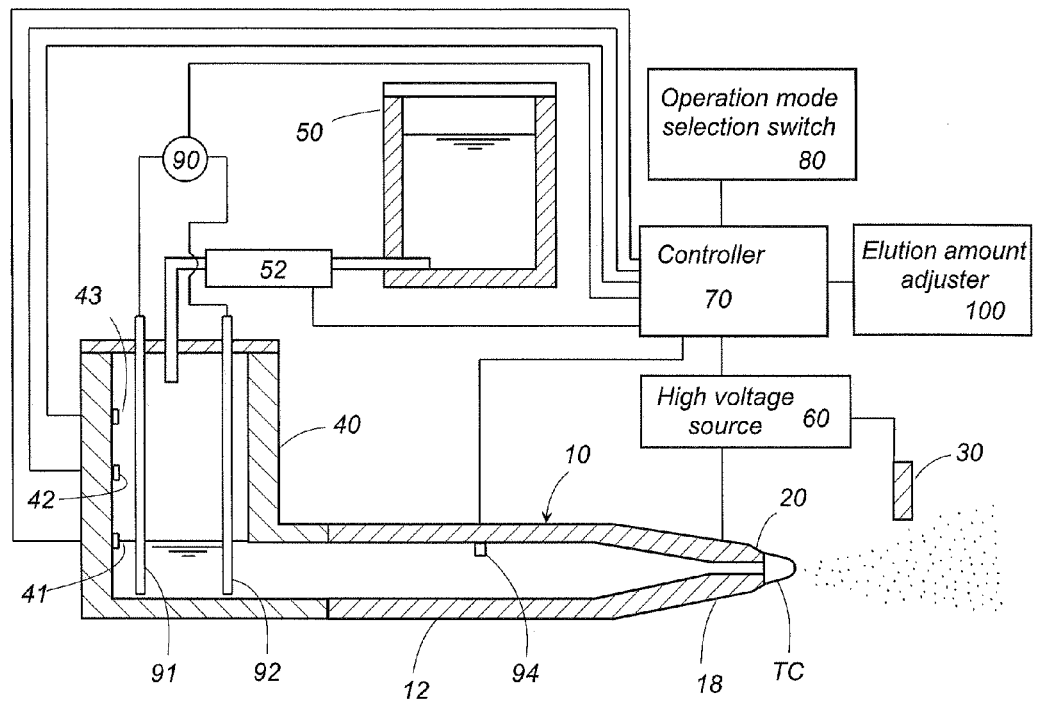
FIG. 1 is a schematic diagram illustrating an embodiment of an electrostatically atomizing device of the present invention when operating in a first operation mode.
Figure 2:
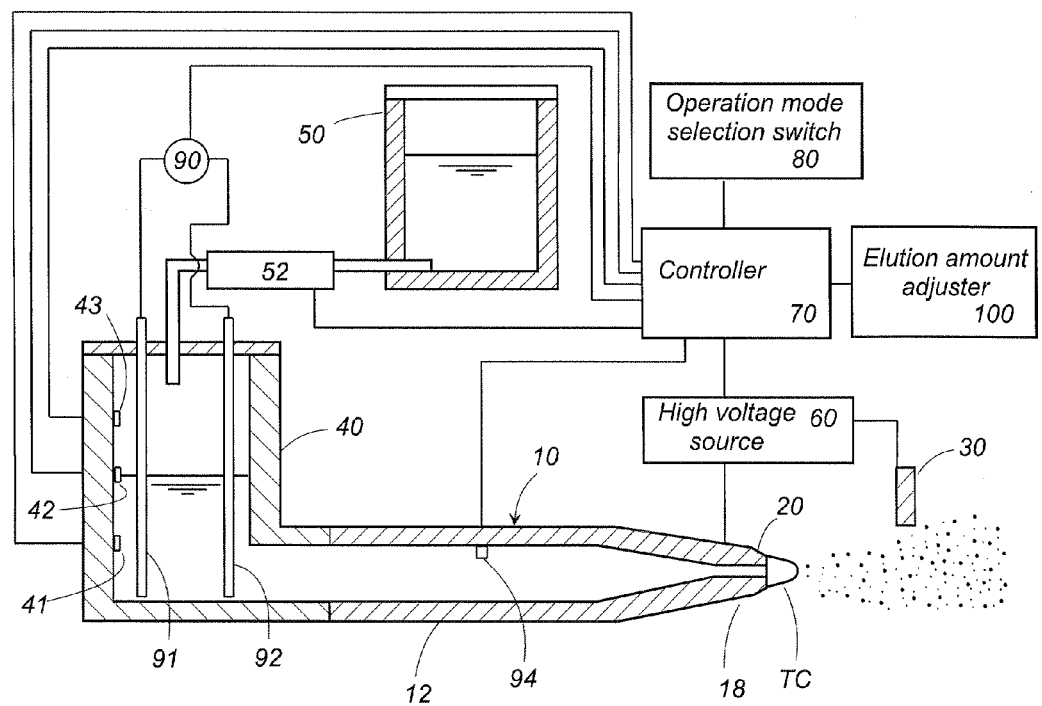
FIG. 2 is a schematic diagram illustrating the embodiment when operating in a second operation mode.
Figure 3:
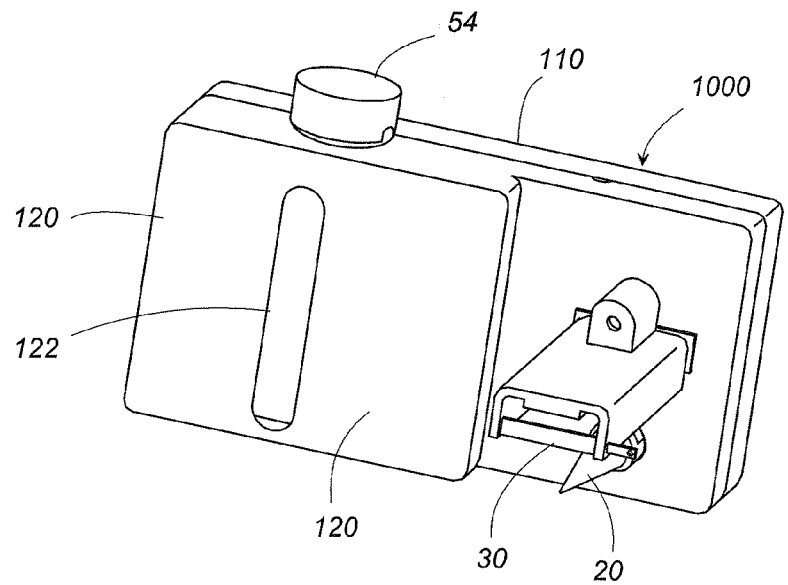
FIG. 3 is a perspective-view diagram of the electrostatically atomizing device according to the embodiment.
Figure 4:
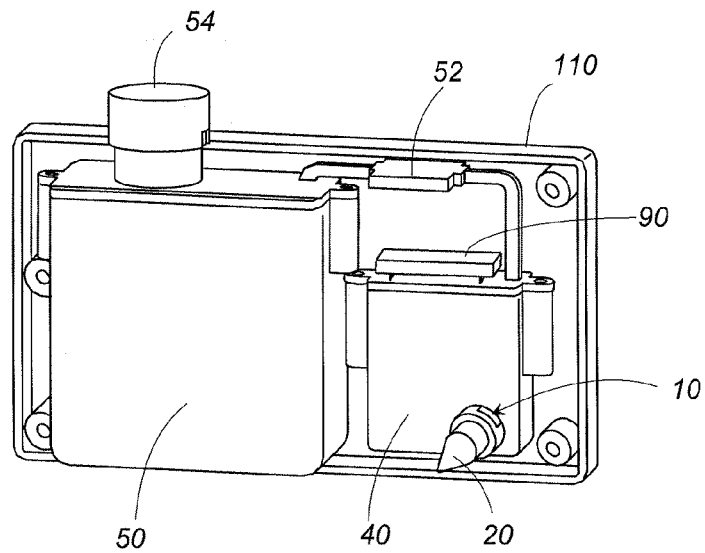
FIG. 4 is a perspective-view diagram of the electrostatically atomizing device according to the embodiment with a cover removed.

An electrostatically atomizing device according to an embodiment of the present invention is explained next with reference to FIGS. 1 and 2. The electrostatic atomizing device, for ejecting a mist of charged minute particles of a liquid, is configured so as to elute sterilizing metal ions into the charged minute particles that are to be ejected.

The electrostatically atomizing device comprises a carrier 10 the tip whereof constitutes an emitter electrode 20; an opposed electrode 30 disposed opposite the emitter electrode; a high voltage source 60 for applying a high voltage between the emitter electrode 20 and the opposed electrode 30; a controller 70; and an operation mode selection switch 80. The purpose of the operation mode selection switch 80 is to select a first operation mode in which there is generated only a mist of nanometer-size (3 nm to 100 nm) charged minute particles, and a second operation mode in which, in addition to a mist of nanometer-size charged minute particles, there is generated also a mist of micrometer-size (0.1 μm to 10 μm) charged minute particles. The operation mode selection switch 80 issues selection instructions to the controller 70. As described below, the controller 70 adjusts the pressure acting on a liquid that is supplied to the tip of the carrier 10, according to the first operation mode or the second operation mode. The controller 70 controls also the high voltage value.

A tank 40 is connected to the rear end of the carrier 10. The liquid such as water stored in the tank 40 is supplied through the carrier 10 to the tip of the emitter electrode 20. The electrostatically atomizing device of the present invention can be used for various kinds of liquids other than water. The present embodiment, however, will be explained on the basis of an example in which water is used as the liquid.

The water supplied to the tip of the emitter electrode 20 forms droplets on account of surface tension. When high voltage, for instance −8 kV, is applied to the emitter electrode 20, there forms a high-voltage electric field between the opposed electrode 30 and the discharge end at the tip of the emitter electrode 20. The droplets become thus electrostatically charged, and are ejected, from the tip of the emitter electrode, as a mist M of charged minute particles. When high voltage is applied between the emitter electrode 20 and the opposed electrode 30, Coulomb forces come into being between the water held at the tip of the emitter electrode 20 and the opposed electrode 30, whereupon a Taylor cone TC forms through local rising of the water surface. Charge concentrates then at the tip of the Taylor cone TC, thereby increasing electric field strength in that section. The generated Coulomb forces generated in that area become greater as a result, causing the Taylor cone TC to grow further. When these Coulomb forces exceed the surface tension of water W, the Taylor cone breaks apart (Rayleigh breakup) repeatedly, generating in the process a large amount of a mist of charged water minute particles, in the nanometer scale. This mist rides the air stream, resulting from ion wind, that flows from the emitter electrode 20 towards the opposed electrode 30, and is ejected through the latter.

A pump 52 replenishes water to the tank 40 from a replenishing tank 50. Water level sensors 41, 42, 43, positioned at different heights, output the level of the liquid in the tank 40 to the controller 70. The controller 70 controls the pump 52 in such a way so as to maintain water level in the tank 40 at the position of a first water level sensor 41 or of a second water level sensor 42, according to the operation mode selected by the operation mode selection switch 80.

The carrier 10 is shaped as a tube. The leading end of the carrier 10, which forms the emitter electrode 20, is a capillary tube 18. The inner diameter of the portion of the carrier 12 that extends from the tank 40, at the rear end, up to the emitter electrode 20, at the leading end, is set in such a manner so as to preclude capillarity, and in such a manner that the hydraulic head of water in the tank 40 acts on the water droplets supplied to the tip of the emitter electrode 20. The inner diameter of the tip of a main tube 12 decreases gradually towards the leading end thereof, where a capillary tube is formed. Water forms droplets by surface tension at the tip of the emitter electrode, which is a capillary tube. The positions of the first water level sensor 41, the second water level sensor 42 and the third water level sensor are set so as to deliver a hydraulic head that does not hinder formation of water droplets by surface tension. This hydraulic head acts on the Taylor cone TC that forms through application of a high voltage.

The center axis of the carrier 10 is disposed horizontally, while the tank 40 coupled to the rear end of the carrier 10 has height in the vertical direction. As illustrated in FIG. 1, the first water level sensor 41 is formed at the minimum water level required for filling the carrier 10 with water and eliciting a minimum hydraulic head that acts on the Taylor cone TC. The second water level sensor 42 is disposed above the first water level sensor 41, as illustrated in FIG. 2, eliciting a predetermined hydraulic head that is higher than the minimum hydraulic head. The third water level sensor 43 determines the maximum allowable hydraulic head. The minimum hydraulic head is a value for which only a mist of nanometer-size charged minute particles forms through high-voltage induced breakup at the tip of the Taylor cone TC. The predetermined hydraulic head is the pressure for which there form micron-size charged minute particles, in addition to the mist of nanometer-size charged minute particles, through breakup at portions other than at the tip of the Taylor cone TC. The controller 70 stops the pump 52 in case the water level rises above the second water level sensor 42 and reaches the third water level sensor 43. The shape of the Taylor cone TC is maintained on account of surface tension. Through the action of the above-described predetermined hydraulic head, however, part of the surface of the Taylor cone breaks and flies apart, through application of a high voltage, at surface portions outside the forwardmost end of the cone, where charges concentrate. Charges do not concentrate at portions outside the forwardmost end to the degree that they do at the forwardmost end, and hence the breakup energy of water is smaller at such portions. This is believed to result in the formation of mainly a mist of micron-size charged minute particles.

Therefore, applying a high voltage while a predetermined hydraulic head acts on the water supplied to the tip of the emitter electrode 20, as described above, causes a mist of nanometer-size charged minute particles to form through breakup at the tip of the Taylor cone TC, and a mist of micron-size charged minute particles to form through breakup at portions other than the tip of the Taylor cone TC. These mists are ejected, diffused into each other, into a space. The mists are generated continuously since water is supplied ongoingly to the emitter electrode 20.

The mist of nanometer-size charged minute particles comprises active species (radicals). These active species sterilize, deodorize or decompose harmful substances that are present in the space. The micron-size charged minute particles diffuse through the space, humidifying the latter.

The hydraulic head acting on the emitter electrode 20 is caused to vary between that of the first water level sensor 41 and that of the third level sensor 43 by providing other water level sensors in addition to the water level sensors above. Doing so allows adjusting the particle size distribution of the mist of nanometer-size charged minute particles and the mist of micron-size charged minute particles, and adjusting the proportion between the mist of nanometer-size charged minute particles and the mist of micron-size charged minute particles.

The tank 40 comprises a pair of metal bodies 91, 92, of different metals, the lower end of each metal body being immersed in water. Ag, Zn, or Cu is used as the metal. Ag, Zn, or Cu elutes metal ions having sterilizing power. The present embodiment uses Ag and Cu metal bodies, such that Ag+metal ions are eluted into the water in the tank 40 by applying a voltage between the Ag and Cu metal bodies using a voltage applicator 90. As a result, the metal ions are taken up by the charged minute particles that are ejected from the tip of the emitter electrode 20, and are released into the environment space. Sterilization of the environment space is enhanced thereby through the combined action of the metal ions and of the active species (radicals) comprised in the charged minute particles. In particular, the metal ions adhere to substances that are present in the environment space, persisting therein for a long time. As a result, harmful substances and germs that intrude into the environment space can be effectively removed after release of the mist of charged minute particles.

The elution amount of metal ions varies in accordance with the voltage applied by the voltage applicator 90 between the metal bodies 91, 92. The elution amount is adjusted by an elution amount adjuster 100. The controller 70 controls the voltage applicator 90 in such a way so as to generate voltage corresponding to the value set by the elution amount adjuster 100, to elute thereby a predetermined amount of metal ions into the water in the tank 40.

The electrostatically atomizing device comprises a conductivity sensor 94 for measuring the conductivity of the liquid ejected from the emitter electrode 20. The controller 70 varies the voltage applied between the metal bodies 91, 92 on the basis of the measured conductivity, to elute thereby metal ions in the amount set by the elution amount adjuster 100. The elution amount of metal ions depends on the conductivity of the liquid that is ejected from the emitter electrode 20. Therefore, the metal ions can be eluted in a desired amount, regardless of the type of liquid used, by varying the voltage applied between the metal bodies in accordance with the conductivity. When the number of types of liquid used is set to one beforehand, the conductivity sensor and the control function that is based on the conductivity sensor can be omitted. In addition to being provided inside the carrier 10, as illustrated in the figure, the conductivity sensor 94 may also be provided in the tank 40.

The above-described embodiment illustrates an example in which $Ag^+$ ions are eluted. The present invention, however, is not necessarily limited to $Ag^+$ ions alone. The invention may use $Cu^+$, $Zn^+$ or other metal ions, with the combinations of the two types of metal bodies being selected depending on the desired metal ion types.

Also, the above described embodiment illustrates an example that the first operation mode and the second operation mode are selected. However, the present invention is not limited to the above described embodiment. The electrostatically atomizing device may operate in either operation mode alone, or in such a manner so as to generate micron-size charged minute particles, by increasing the pressure acting of the tip of the emitter electrode. In all cases, metal ions are taken up by the generated charged minute particles, so that the metal ions are released into the environment space, affording thereby a high sterilizing effect.

The various components that make up the electrostatically atomizing device are assembled in a housing 1000, as illustrated in FIGS. 3 and 4. The housing 1000 comprises a base 110 and a cover 120 that covers the base 110. The carrier 10 integrated as a single unit with the tank 40, the replenishing tank 50 and the pump 52 are attached to the base 110, while the opposed electrode 30 is held at the cover 120. The emitter electrode 20 and the opposed electrode 30 are exposed outside the housing 1000. The electric components that make up the high voltage source 60, the controller 70 and the elution amount adjuster 100 are disposed in the housing 1000. A window 122 is formed in the cover 120, such that the water level in the replenishing tank 50, formed of a transparent material, can be checked through the window 122. The replenishing tank 50 is provided with a cap 54 through which water can be topped up as required.

FIG. 5 illustrates another embodiment of the present invention, identical to the above-described embodiment except that herein the voltage applicator 90 and the function for controlling the voltage applicator 90 have been removed. Therefore, identical members are denoted with identical reference numerals, and recurrent explanations are omitted. In the present embodiment, two types of metal bodies 91, 92 having different ionization tendencies are electrically connected outside the tank 40, so that metal ions from one of the metal bodies are eluted into the liquid in the tank 40 on account of the potential difference that forms between the two metal bodies.

The invention claimed is:

1. An electrostatically atomizing device including a metal ion elution means for eluting sterilizing metal ions into a liquid to be electrostatically atomized, wherein said device comprises a tank configured to hold a volume of said liquid, and a carrier connected to said tank to be supplied with said liquid and to feed the liquid to a discharge end where said liquid is atomized by application of a high voltage, and wherein said metal ion elution means comprises a set of different metal bodies immersed into the liquid in said tank to give a potential difference between said metal bodies for eluting said metal ions, said tank being configured to hold the volume of said liquid so that a liquid level of said liquid has a height which is a predetermined height or more, said metal bodies being arranged to have their lower ends located below said liquid level, whereby said metal bodies are kept immersed in said liquid of said tank, wherein a leading end of said carrier which forms an emitter electrode is a capillary tube, and wherein an inner diameter of a portion of said carrier that extends from the tank, at a rear end, up to the emitter electrode, at the leading end, is set in such a manner so as to preclude capillarity.

2. The electrostatically atomizing device as set forth in claim 1, wherein one of said metal bodies which elutes said metal ions in said liquid is selected from a group consisting of Ag, Zn, and Cu.

3. The electrostatically atomizing device as set forth in claim 1, wherein said metal elution means comprises a voltage applicator which gives said potential difference between said metal bodies.

4. The electrostatically atomizing device as set forth in claim 3, wherein said voltage applicator provides a varying voltage between said metal bodies for regulating an elution amount of said metal ions.

5. The electrostatically atomizing device as set forth in claim 3, further including:

means configured to measure conductivity of said liquid, said voltage applicator being configured to vary a voltage difference between said metal bodies in accordance with the measured conductivity of said liquid for regulating the elution amount of said metal ions.

6. The electrostatically atomizing device as set forth in claim 1, wherein when the liquid is atomized by the application of the high voltage, a mist of charged minute water particles which contains active species and also the metal ions is generated.

* * * * *